United States Patent [19]
Rizza et al.

[11] Patent Number: 5,529,918
[45] Date of Patent: Jun. 25, 1996

[54] PROCESS FOR PREPARING NEURAMINIDASE

[75] Inventors: Victor Rizza, Siracusa; Umberto Scapagnini, Battiati, both of Italy

[73] Assignee: Fidia S.p.A., Abano Terme, Italy

Related U.S. Application Data

[63] Continuation-in-part of PCT/EP92/02868 published as WO93/12223

[21] Appl. No.: 267,012

[22] Filed: Jun. 15, 1994

[30] Foreign Application Priority Data

Dec. 17, 1991 [IT] Italy ................... MI91A3375

[51] Int. Cl.$^6$ ........................................... C12N 9/24
[52] U.S. Cl. .................. 435/200; 435/252.1; 435/830
[58] Field of Search ........................... 435/200, 252.1, 435/830

[56] References Cited

U.S. PATENT DOCUMENTS

| | | | |
|---|---|---|---|
| 4,071,408 | 1/1978 | Flashner et al. | 435/200 |
| 4,710,470 | 12/1987 | Uwajima et al. | 435/200 |
| 5,116,752 | 5/1992 | Sugimori et al. | 435/200 |

OTHER PUBLICATIONS

J. Bacteriology, vol. 136, No. 3, pp. 874–879 (1978).
J. Biochem. 82, pp. 1452–1433 (1977).

*Primary Examiner*—Herbert J. Lilling
*Attorney, Agent, or Firm*—Hedman, Gibson & Costigan

[57] ABSTRACT

Process for preparing neuraminidase, by using as the bacterial strain the Arthrobacter Sp in a culture containing low concentrations of N-acetyl-neuraminic acid.

13 Claims, 5 Drawing Sheets

000001
PROCESS FOR PREPARING NEURAMINIDASE

This application is a continuation-in-part of international PCT Application No. PCT/EP92/02868, filed Dec. 11, 1992. The applicants hereby claim the priority of PCT Application No. PCT/EP92/02868 under 35 U.S.C. §365(c) and 35 U.S.C. §120.

BACKGROUND OF THE INVENTION

The invention relates to an improved process for preparing neuraminidase, an enzyme playing a leading role as a tool for the biological research, for the studies concerning the cellular facies and for the enzymatic analysis of glycoproteins.

PRIOR ART

Former experimental works did show that neuraminidase is an exocellular enzyme, very important because it can modify the proteins and hydrolize, more particularly, the residua of sialic acid, localized in the terminal positions of glycolipids, in particular of glycosphingolipid GDia.

Neuraminidase is widely distributed throughout viruses and microorganisms. This enzyme, in fact, is contained in all viruses of the mixovirus group and in the bacteria like *Arthrobacter sialaphilus, Vibrio choleral, Clostridium welchii* (perfringens), *Pseudomonas fluorescens, Ps. stuzeri, Ps. pyocyaneus, Lactobacillus bifidus,* Pneumococcus and *Diphteroid bacilli* and *Klebsiella aerogenes.*

The preparation of neuraminidase starting from said viruses and bacteria requires, however, complex media and complex operative conditions, leading to a poor enzyme output.

SUMMARY

The Applicant found an improved process allowing an industrial preparation of neuraminidase; such process comprises the use of a bacterial strain having a rapid aerobian growth in a cheap medium, thus obtaining a high yield, without any appreciable presence either of toxins or of proteolytic enzymes.

Said process is employing, as the bacterial strain, the Arthrobacter Sp, obtained from the modification of the Arthrobacter Urefaciens ATCC 7562, and comprises the following steps:

a) Arthrobacter Ureafaciens ATCC 7562 is grown on a solid agar medium in the presence of N-acetyl-neuraminic acid and casein hydrolysate, thus obtaining an axenic consisting of a small glossy brilliant colony, herein defined as Arthrobacter Sp;

b) a culture of the above obtained Arthrobacter Sp is grown in a liquid medium containing NANA, in a concentration comprised between 0.1 and 1%, and casein hydrolysate;

c) once steady state conditions are reached, the culture of Arthrobacter Sp. is made to occur under chemostasis conditions, feeding it with a fresh medium which contains NANA and is free from casein hydrolysate, thus obtaining the production of a considerable amount of neuraminidase;

d) the thus obtained neuraminidase is recovered from the media and purified by means of filtration followed by concentration, ultrafiltration, dialysis, and flow through an ion exchange resin. It is worth noting that the presence of NANA is essential for enzyme output.

BRIEF DESCRIPTION OF THE INVENTION

DETAILED DESCRIPTION OF THE INVENTION

Figure 1:
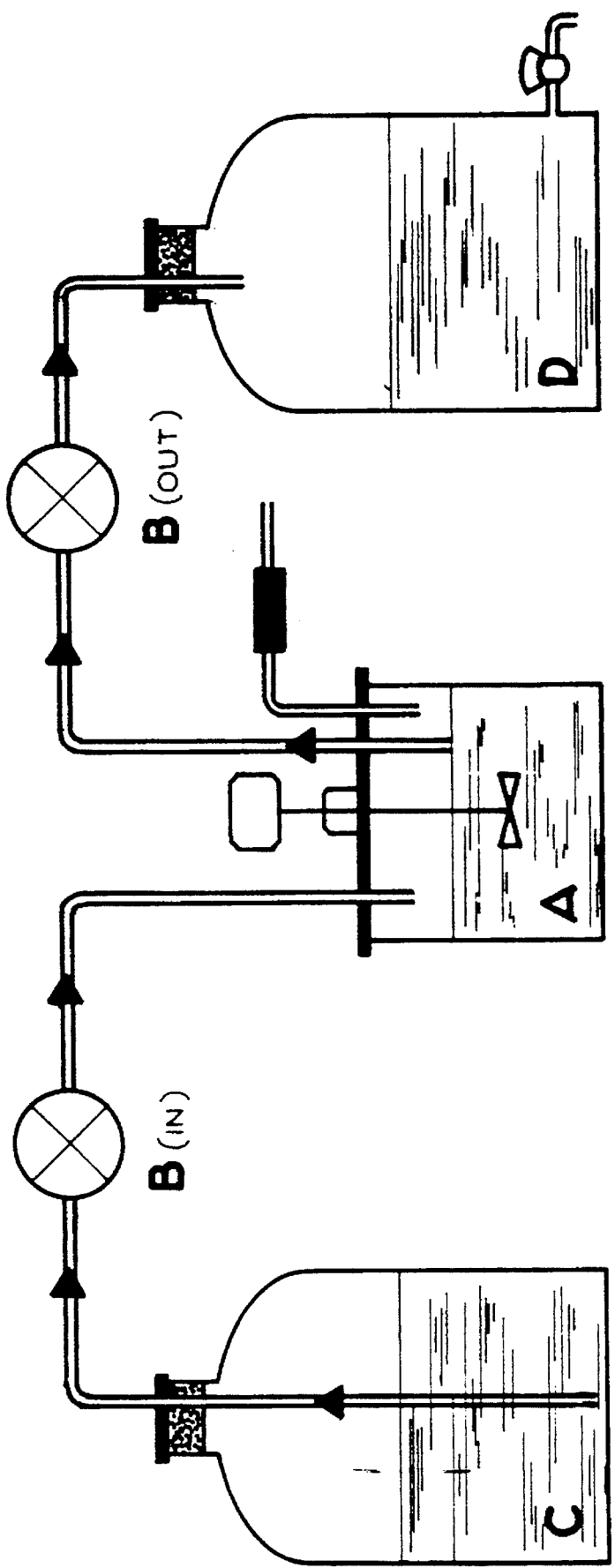
FIG. 1 is a schematic diagram of an apparatus for the practice of the invention.

The features and the advantages of the process for the preparation of neuraminidase, employing as the bacterial strain the Arthrobacter Sp according to the present invention, will be more widely illustrated during the following detailed description. The original microorganism, used during the tests, was the Arthrobacter Urefaciens ATCC 7562, purchased from the American Type Culture Collection.

This microorganism was then modified by growth in a solid medium containing casein hydrolysate (0.1%), N-acetyl-neuraminic acid (NANA) and agar (typically at pH comprised between 7.0 and 7.5, and preferably 7.3, and at temperatures comprised between 25° and 30° C.). The growth of the microorganism, in the presence of NANA, is performed by means of several passages, thus obtaining an axenic consisting of a small glossy brilliant colony, defined as Arthrobacter Sp. The strain Arthrobacter Sp. was deposited on Apr. 11, 1995 as *Arthrobacter ureafaciens* VR-1, NCIMB 40717 at: "The National Collections of Industrial and Marine Bacteria Limited", 23 St Machar Drive, Aberdeen AB2 1RY, Scotland, UK and the deposit was made under the provisions of the Budapest Treaty.

*Arthrobacter ureafaciens* ATCC 7562 produces on the above solid medium tiny, round colonies with a characteristic yellow-amber color. After two or three days of growth on solid medium, the colonies began to deform and produce a waxy polymer-like substance which gives the colony a creamy appearance.

When these colonies are replated they return to the original colony morphology (small, round) and with increasing incubation times they develop into large creamy colonies.

The colony of the Arthrobacter Sp. used in the present invention was isolated approximately 24 hours after growth on solid medium according to step a) and was chosen because it developed precociously as compared to the rest of the colonies.

Further, when in presence of other colonies, its colony looked larger and showed a more brilliant and intense yellow-amber color. Arthrobacter Sp. shows a feature residing in a high output of neuraminidase, when it is grown in a liquid medium in the presence of low concentrations of NANA (0.1–1%).

It has to be noted that the precursor strain, Arthrobacter Urefaciens ATCC 7562, doesn't give rise to any output of neuraminidase, when exposed to NANA.

The isolated Arthrobacter Sp. also exhibits the following characteristics:

1. Production of neuraminidase isoenzyme active on GDia substrate.

2. Small gram negative rod which undergo rod-sphere-rod morphogenesis during cultivation in liquid medium.

3. It produces a bright yellow pigment during growth on liquid medium.

4. It grows on glucose, gluconate, fructose and succinate.

5. When grown on glucose, the neuraminidase production is inhibited.

The medium typically used for the growth of the Arthrobacter Sp according to step b) of the present process is an aqueous solution comprising casein hydrolysate, NANA and salts (such as dibasic ammonium phosphate, potassium (monobasic) phosphate ($KH_2PO_4$), sodium chloride, magnesium sulphate, ferrous sulphate). Optionally, yeast extract may be present.

According to preferred conditions of the present invention, the concentration of NANA during step b) is comprised between 0.1 and 1% (g/100 ml), and the concentration of casein hydrolysate is comprised between 0.1 and 0.5% (g/100 ml).

In step c), the concentration of NANA typically varies from 0.05 to 1%.

The culture of Arthrobacter Sp., both under batch conditions such as those of step b) and under chemostasis conditions such as those of step c), is carried out under stirring-aeration conditions, at pH values comprised between 7.0 and 7.5 and at temperatures comprised between +20° C. and +30° C.

Preferably, the pH is adjusted at 7.3 and the temperature is equal to 26° C.

Steady state (stationary phase) conditions represent a growth state in which, after the logarithmic growth phase, the rate of cell division and the one of cell death are in equilibrium, thus a constant concentration of microorganism is maintained in the vessel. Stationary state conditions can be simulated under chemostasis conditions, maintaining an equilibrium state between cell doubling $\mu$ and wash out rate D, wherein $\mu=D$ e $dx/dt$ is 0 [$\mu$ represent the specific growth rate (1/x) (dx/dt), wherein x is the concentration of microorganism in vessel and t is time; (D is dilution rate or number of complete volume changes per unit time)].

According to the present process, steady state conditions are spontaneously reached after the logarithmic growth phase at the end of step b), then they are maintained under chemostasis conditions, by feeding the fresh medium into the reaction vessel.

Preferably, steady state conditions are reached at the end of the logarithmic phase (step b) when the optical density of the cells in the reaction medium reaches values comprised between 1.5 to 4 O.D., and maintained during step c) by feeding fresh medium into the reaction vessel at a rate so as to maintain the optical density (O.D.) between 3 and 5 units.

It is worth noting that according to the present process the maximum neuraminidase output occurs during the steady state of cells growth. According to a typical embodiment of the present invention, in step b) the used medium for the growth of the Arthrobacter Sp. contains the following ingredients in aqueous solution: casein hydrolysate, yeast extract, NANA, dibasic ammonium phosphate, potassium (monobasic) phosphate ($KH_2PO_4$), sodium chloride, magnesium sulphate, ferrous sulphate (pH 7.3; temperature 26° C.).

By working under such conditions, steady state conditions are reached after 40–60 hours of cultivation.

Typically, the fresh medium can be fed into the reactor vessel when the bacterial mass reaches the value of 0.4 g/l.

According to Examples 1–3, as the bacterial mass reaches the value of 0.4 g/l, it is added to the culture some fresh medium, containing 0.5 g/l of NANA and free from casein hydrolysate, the flow rate corresponding to a dilution value (number of volume changes per time unit) equal to 0.13 $h^{-1}$ (thus completely replacing the the medium of step b) in a 7–8 hours period).

By working under such conditions, a considerable amount of neuraminidase is produced and is accumulated in the broth. According to a particularly preferred embodiment of the present invention, step b) is carried out using as the growing medium for Arthrobacter Sp. an aqueous solution containing casein hydrolysate and NANA as the only carbon sources and step c) is carried out using a fresh medium containing yeast extract other than NANA as the organic nutrients.

Preferably, the medium used in step b) contains casein hydrolysate and NANA both in a 0.5% amount, while the medium used in step c) contains 0.5% of NANA and 0.4% of yeast extract.

Both step b) and c) are preferably carried out at pH 7.3, at 26° C. When the process is carried out according to this preferred embodiment, state steady conditions corresponding to optical density values comprised between 2.0–2.5, more preferably 2.5, are reached during step b) after 18–20 hours of cultivation. During step c), the continuous culturing cultivation are started by feeding the above mentioned fresh medium into the reaction vessel when the optical density fluctuates between 1.4 and 2.5, and said fresh medium is fed at a flow rate so as to raise and maintain the optical density between 4 and 5 O.D, more preferably at 5 O.D. units.

The fresh medium was preferably fed at a flow rate comprised between 27 to 35 ml/min, which allowed the liquid culturing medium (10 l) contained in the reactor vessel during phase b) to be completely replaced in a 6–7 hours period. Higher flow rates generally led to a decrease in enzyme out put, because the wash out rate of cells was higher than cell doubling time, while flow rates less than 27 ml/min increased cell growth rate, but decreased enzyme output.

It is worth noting that under these conditions stationary phase of cell growth could be maintained indefinitely.

Under such preferred conditions, a surprisingly high neuraminidase output (up to 7000 U/l after 18 hours) is obtained also during step b), before shifting to the continuous culturing conditions, and what is even more surprising, the neuraminidase output during step c) reaches 11,000–12,000 U/l. Both these values are well higher than those obtained according to the prior art processes.

Further, this high neuraminidase production can be maintained as long as desired, for period even longer than 220 hours.

The experimental results relating to the present process suggest that presence of casein hydrolysate in the growth medium of step a) is important to obtain elevated O.D. values.

Further, the Applicants deem that the addition of yeast extract, a rich nitrogen source, to the growth medium used for the chemostasis cultivation according to step c), made the microbial cells more quiescent, facilitated reaching steady-state conditions more easily and allowed maintainance of this steady state for extended periods of time.

The used apparatus is illustrated in FIG. 1. It consists of a continuous flow system, traded by the New Brunswick Instrument Co. as MICROGEN-GEN II SYSTEM, wherein A is the reactor (or culture container), C is the vessel containing the fresh medium, D is the tank containing the product and B(in) and B(out) are the pumps fit fop respectively feeding the media to the reactor and for pumping the product from the reactor to the tank D.

The reactor A (14 liters) is inoculated by an initial culture of Arthrobacter Sp; the optical density of the cellular suspension is comprised between 0.1 and 0.2 OD units. The cellular subdivision begins after a lag phase of 5–7 h. The average exponential or logarithmic growth phase is reached after 14 h and the doubling time of the cellular subdivision is 4.6 h.

According to Examples 2 and 3, the steady state conditions are established as the cells reach an optical density between 3 and 4 OD units.

The steady state of the culture is maintained by feeding the fresh sterile medium into the reaction flask, the flow rate being substantially equal to 1.8 l/h. The following examples are supplied fop merely illustrative purposes and do not limit in any case the scope of the invention.

EXAMPLES

Growth of Arthrobacter Ureafaciens ATCC 7562 in a Solid Medium in the Presence of Casein Hydrolysate and N-acetyl-neuraminic Acid and Isolation of Arthrobacter Sp.

Arthrobacter Ureafaciens ATCC 7562 was grown on Petri plates, in a solid medium having the following composition: casein hydrolysate 1.0 g; yeast extract 0.5 g; NANA 1.0 g; $(NH_4)_2PO_4$ 2.0 g; $KH_2PO_4$ 1.0 g; NaCl 3.0 g; $MgSO_4$ 0.1 g; $FeSO_4$ 0.02 g; Agar (DIFCO) 20.0 g; $H_2O$ 1 liter.

After 24 hours of incubation (pH 7.3; 30° C.) a small glossy brilliant colony was isolated, designated as Artrhobacter Sp.

The colony of Arthrobacter Sp. developed precociously with respect to the rest of colonies. When in the presence of other colonies, it appeared as a single isolated colony, larger and with a more developed yellow-amber color in respect of the colonies in its vicinity.

Materials

In Examples 1, 2 and 3, the medium used to grow Arthrobacter Sp. during step b) of the present process was an aqueous solution containing casein hydrolysate and NANA in the amounts indicated for each example, yeast extract (0.05%) and salts: dibasic ammonium phosphate (0.2%), potassium (monobasic) phosphate ($KH_2PO_4$) (0.1%), sodium chloride (0.3%), magnesium sulphate (0.1%), ferrous sulphate (0.02%). pH was 7.3 and the temperature was equal to 26° C.

EXAMPLE 1

Bacterial Growth According to a NANA Concentration Equal to 0.1%

The Arthrobacter Sp was made to grow in a medium together with a 0.1% concentration of casein hydrolysate and with a 0.1% of NANA. Once the steady state level was reached, a fresh medium was fed to the reactor; such medium contained 0.05% of NANA and salts and was free from casein hydrolysate. The flow rate was 30 ml/minute and the dilution rate (number of volume exchanges per time unit) was equal to 0.13 $h^{-1}$.

Figure 2:
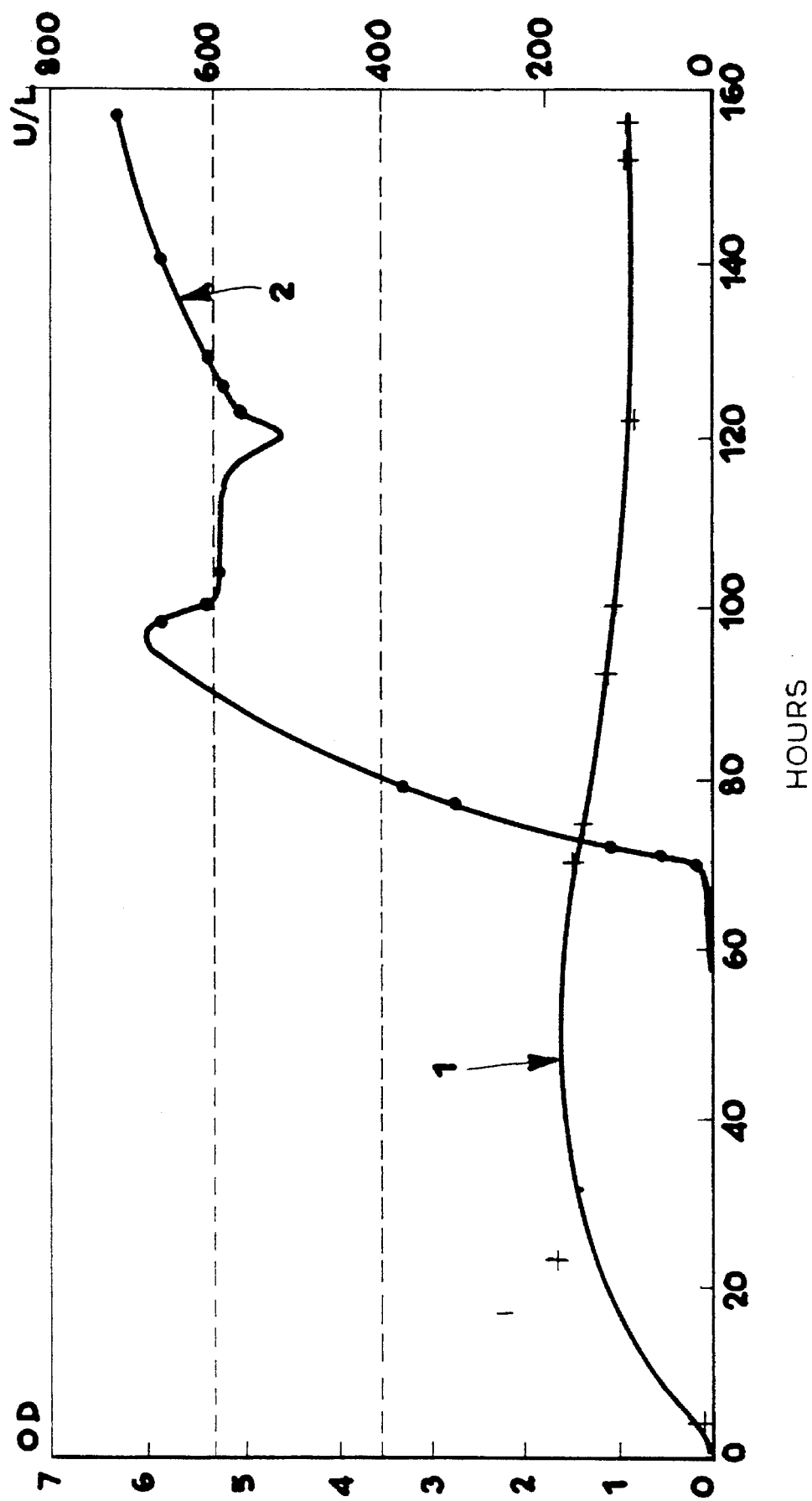
FIG. 2 is a graph which shows the growth rate versus time for Example 1.

The results of this preparation are recorded on FIG. 2, where it is possible to note an enzyme output approximately equal to 700 Units/l during the steady-state (one Enzyme Unit is an amount of enzyme sufficient for hydrolizing 1 μmol/minute of NANA, at pH 5.3 and at 37° C., while employing GDia as the substrate). In said figure, line 9 represents the optical density (OD), whereas line 2 represents the enzymatic activity (U/L).

EXAMPLE 2

Bacterial Growth When the NANA Concentration is 1% The Arthrobacter Sp is made to grow in a medium containing 0.1% of casein hydrolyzate and 1% of NANA.

Once the bacterial growth attained the steady state, the reactor was fed with a fresh medium (containing 0.05% NANA and salts), free from casein hydrolysate; the flow rate (of the fresh medium) was 30 ml/minute.

Figure 3:
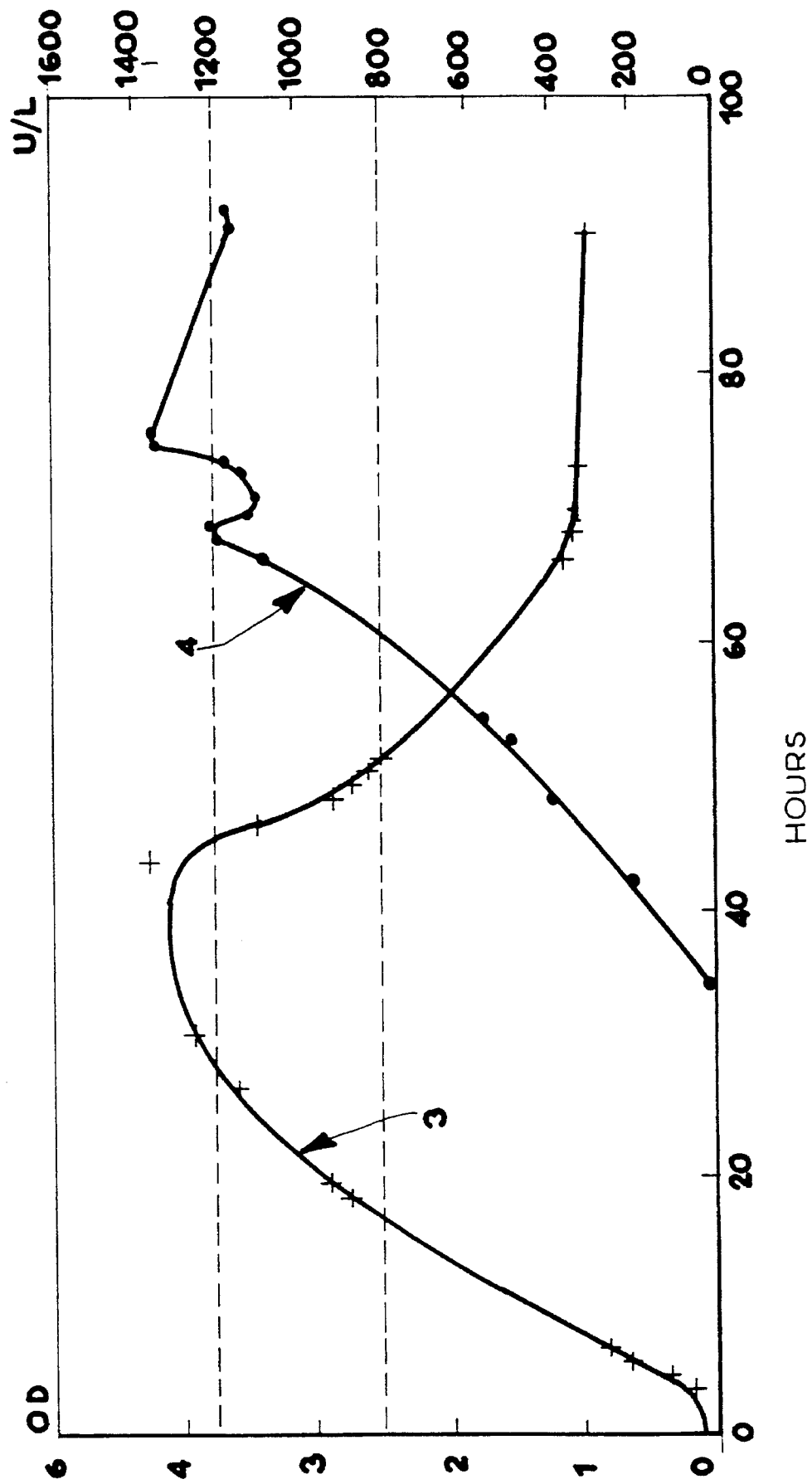
FIG. 3 is a graph which shows the growth rate versus time for Example 2.

The results were recorded on FIG. 3 and show a steady state output of approximately 1400 units/l. Line 3 expresses the optical density (OD) and line 4 expresses the enzymatic activity (U/L).

EXAMPLE 3

Bacterial Growth When the NANA Concentration is 0.1%

The Arthrobacter was made to grow in a medium containing 0.5% of casein hydrolysate and 0.1% of NANA.

Figure 4:
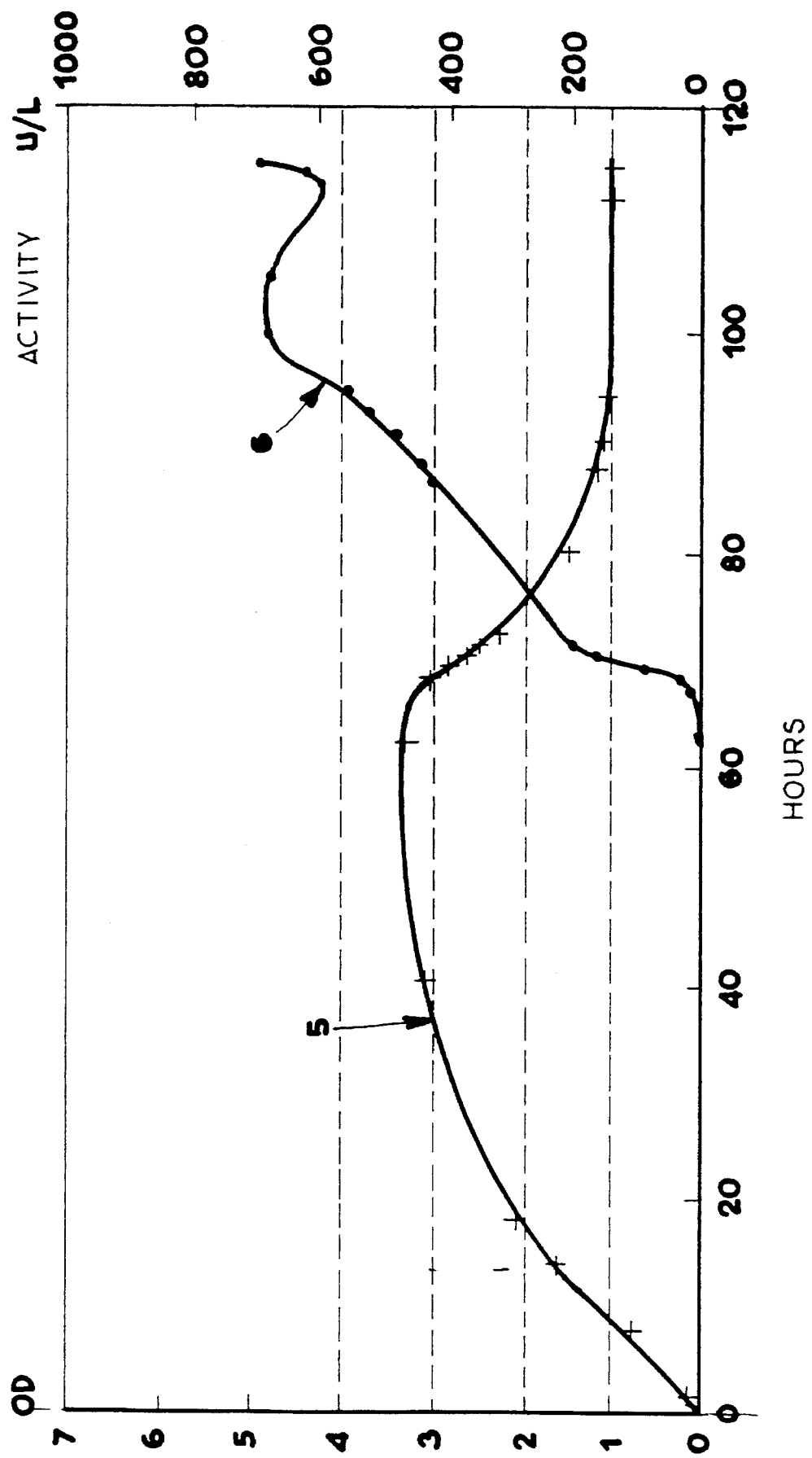
FIG. 4 is a graph which shows the growth rate versus time for Example 3.

Once the steady state of the bacterial growth was reached, the reactor was fed with a fresh medium containing 0.05% of NANA and salts, free from casein hydrolysate; the flow rate was 30 ml/minute. The results are recorded on FIG. 4 and show, in correspondence to the steady state, an enzyme output of about 800 Unit/l.

In said figure, line 5 represents the optical density (OD) and line 6 represents the enzymatic activity (V/L).

EXAMPLE 4

The Arthrobacter Sp. was made to grow in a liquid aqueous medium containing 0.5% casein hydrolysate; 0.5% NANA and salts: $(NH_4)_2PO_4$ 0.2%; NaCl 0.3%; $KH_2PO_4$ 0.1%; $MgSO_4 \cdot 7H_2O$ 0.1%; $FeSO_4 \cdot 7H_2O$ 0.002%, at 26° C. During cells growth, pH fluctuates and is adjusted to 7.3.

After 18–20 hours the stationary phase (steady state) conditions were reached (O.D.=2.5 units) and an extremely high out put of neuraminidase was observed (about 7000 U/l after 18 hours).

O.D. slowly decrease from 2.5 and 1.4 and, after 32 hours, cells were shifted from batch culture to continuous culturing conditions, feeding the reactor with a fresh medium containing 0.4% yeast extract, 0.5% NANA and salts, at flow rates between 27 and 35 ml/minute.

Under these conditions, 6–7 hours were necessary for changing one vessel volume, thus completely replacing the initial medium.

This flow rate sustained a constant cell growth rate corresponding to O.D. values comprised between 3 and 5 units.

Figure 5:
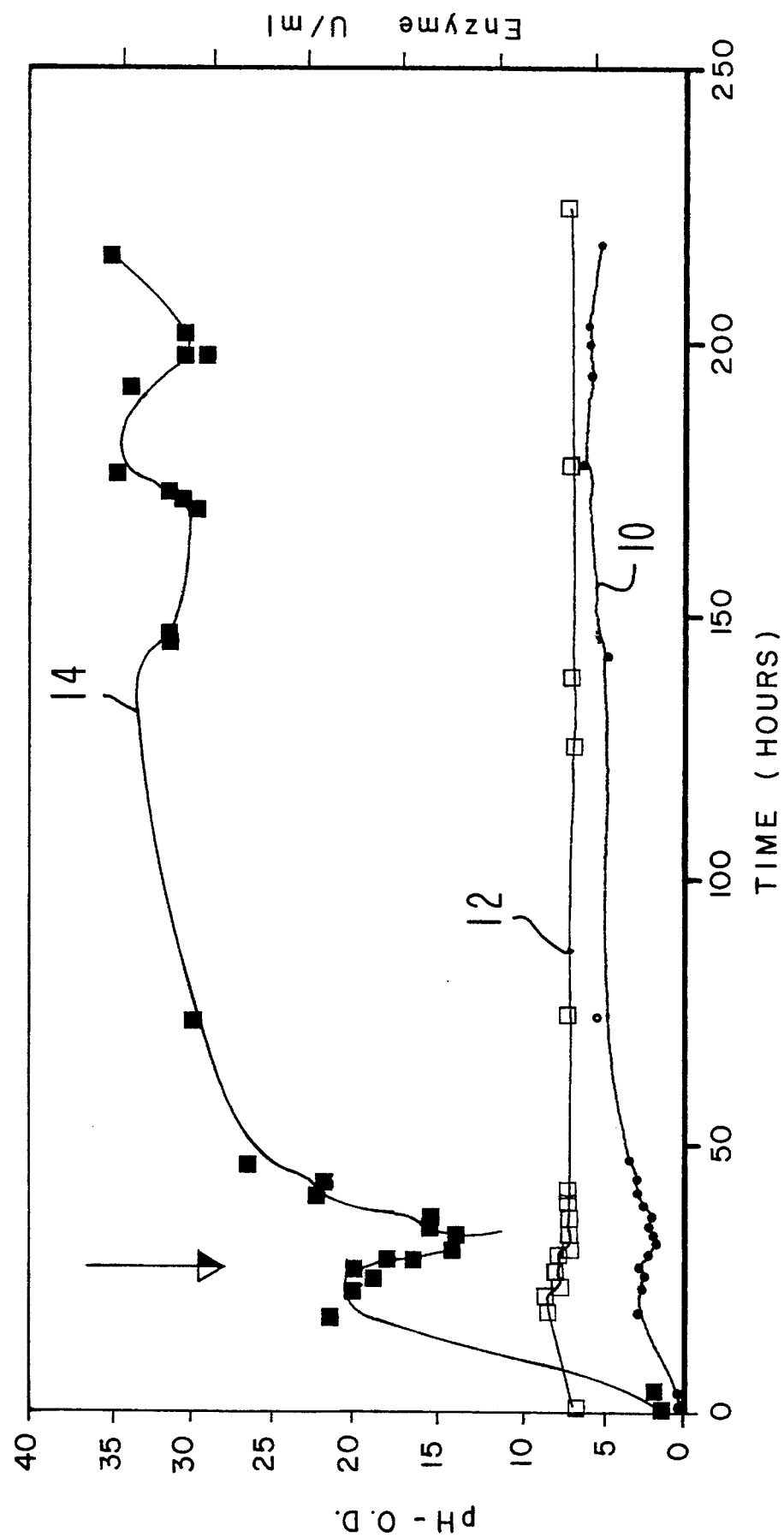
FIG. 5 is a graph which shows the growth rate versus time for Example 4.

Under these conditions, an enzyme output comprised between of approximately 10,000 and 11,000 U/l was observed (see Table I). These steady state conditions, corresponding to an extremely high neuraminidase production, were maintained in this example for about 10 days, but could have been extended indefinitely longer. Table I reports the cell density, the enzyme output and the flow rate of fresh medium during 180 hours of Arthrocabter Sp. cultivation. FIG. 5 reports the data relating to the cultivation over a period of about 220 hours.

Ths start of the continuous culturing condiitons are illustrated by the double asterisk in the Table or the arrow in FIG. 5. Curve 14 represents the senzyme in U/ml, curve 12 represents the pH amd curve 10 represents the O.D. at 660 nm.

According to Table I, neuraminidase production was lower during lag phase and logarithmic phase (470–720 U/l in the first 12 hours). Then, it dramatically increased up to 7000 U/l when the cells growth entered the stationary phase. As the stationary phase proceeds, enzyme activity decreases to 4000 U/l during the 20–30 hours period. Such a decrease is accompanied by a decrease in O.D., which is common during late stationary phase when cell death rate tends to exceed cell doubling rate. After 32 hours, the fresh medium is pumped into the reaction vessel at increasing flow rate, from 11 to 27 ml/min, and both O.D. and enzyme output increase.

TABLE 1

| TIME (hrs) | CELL DENSITY O.D. | ENZYME U/l | FLOW RATE (ml/min) |
|---|---|---|---|
| 0 | — | — | * |
| 3 | 0.2 | — | * |
| 6 | 0.8 | 380 | * |
| 12 | 1.7 | 940 | * |
| 18 | 2.5 | 7,370 | * |
| 20 | 2.1 | 6,400 | * |
| 24 | 2.1 | 5,900 | * |
| 28 | 1.4 | 4,690 | * |
| 32 | 1.4 | 4,280 | 11** |
| 40 | 2.1 | 6,500 | 19 |
| 42 | 2.5 | 7,800 | 26 |
| 50 | 3.6 | 9,750 | 27 |
| 62 | 3.9 | 11,040 | 27 |
| 74 | 4.6 | 10,100 | 28 |
| 140 | 4.8 | 11,000 | 30 |
| 150 | 5.0 | 10,280 | 35 |
| 180 | 6.0 | 10,400 | 35 |

*During the first 32 hours the cells are grown in batch culturing conditions
**Start of conditions culturing conditions is marked by the arrow in FIG. 5 or double asterisk in Table I.

With regard to the neuraminidase purification, according to a preferred embodiment of step d), the filtraiton is carried out on a membrane of cellulose acetate having a pore diameter of 0.2 µm; the concentration is effected through a cellulose acetate membrane showing a molecular cut-off of 10,000 daltons; the dyalisis is effected against a pH 5.3 acetate buffer; and the ion exchange resin has a matrix of dextran cross-linked with epichlorohydrin, functionalised with carboxymethyl groups, and with an exclusion molecular weight limit of $2 \times 10^5$, balanced to pH 5.3 by means of an acetate buffer.

Neuraminidase Purification

The media, collected during the preparation hereinabove, is first of all filtered, in order to separate the microbial cells. This separation is carried out by employing a Sartorius filter, having Sartocon II modules and having a filtering membrane made of cellulose acetate and having a pore diameter of 0.2 µm. The supernatant fluid is then concentrated in a DC10LA or SP20 filter (both supplied by the Amicon Corp. of the U.S.A). The S-10Y10 cartridge (supplied by Amicon), through which the filtrate is made to flow, consists of cellulose acetate, showing a M.W. (molecular weight) cut-off of 10,000 daltons.

The ultrafiltration is then made to occur by means of a Amicon CH2 filter having a S1Y10 cartridge.

While passing through the filter Amicon DC10LA, 220 l of filtrate are approximately reduced to 3 l and while passing through the CH2 filter there is a reduction to 400 ml.

The filtrate is then dialyzed against a pH 5.3 acetate buffer (0.02M), according to the following ratio:

5 volumes of buffer per volume of enzyme.

In our case the Applicant employed 2 l of buffer, in order to dialyze 400 ml of enzyme.

The liltrate is then made to pass through an ion exchanging resin, employing a CM Sephadex C-50 (Pharmacia) (matrix: dextran cross-linked with epichlorohydrin; functional groups: carboxymethyl groups; exclusion Molecular Weight limit of $2 \times 10^5$.) balanced to pH 5.3 by means of a sodium acetate buffer (0.02M). After each purification, the ion exchanging column is regenerated in order to remove the residual proteins, employing 4–5 liters of 1M sodium acetate.

Neuraminidasic Activity Test

1. NANA test.

A few solutions of the blank or standard sample, respectively containing 5, 10, 15 and 20 µg of NANA in 200 µl of water are treated with 10 µl of periodic acid (25 mM in 0.125 N $H_2SO_4$). The mixtures are incubated for 5 minutes at 60° C. and the excess of periodate is then reduced by means of 100 µl of sodium arsenite (1.6% in 0.4N HCl). As the yellow colour of the released iodine gets lost (2 minutes), there is added 1 ml of 0.01M thiobarbituric acid (pH 9) and the sample is covered and heated in a boiling water bath for 7.5 minutes.

The coloured solutions are then cooled by means of an ice-water bath and shaken along with 2 ml of an acetate buffer based on acetone (HCl=2.5%). The extinction level is measured (at 552 nm) by means of a spectrophotometer, against an acetate blank.

2. Determination of the enzymatic activity.

The enzymatic activity of the neuraminidase is determined at the saturation levels of the substrate concentration, corresponding to 5 times the $K_m$ value.

The released product is measured by employing the colorimetric technique (thiobarbituric acid method). For instance, when the neuraminidase enzyme and its substrate (a ganglioside like GDia) are incubated for 5–10 minutes and the NANA, hydrolyzed from the substrate, is employed for evaluating the enzymatic activity, the NANA released in the solution undergoes a series of reactions, in order to determine its actual amount.

Since NANA is also employed for obtaining the culture media of the steady state wherefrom the filtrate is extracted, a few check reactions are carried out, in order to ascertain that the measured NANA be the one coming from the reaction between enzyme and substrate and not the one coming as a residue from the original culture.

For instance, a few tests are carried out on 3 test-tubes, as reported hereinbelow. Each of the test-tubes contains the sodium acetate buffer; moreover the first one contains only GDia substrate (S), the second one [blank (B)] contains only enzyme and the third one contains both substrate and enzyme (E).

|  | S | B | E |
| --- | --- | --- | --- |
| Buffer | 150 | 150 | 100 μl |
| Substrate | 50 | — | 50 μl |
| Enzyme | — | 50 | 50 μl |

In the first test-tube (S) there should be no NANA. Should NANA be retrieved in the second test-tube (B), its spectrophotometric reading is subtracted from the reading obtained from the reaction in test-tube three (E). The enzyme activity is therefore indirectly measured as the amount of hydrolized NANA per minute at pH 5.3 and at 37° C., using GDia as the substrate.

The analysis is performed as follows.

The substrate GDia (50 μl) and the neuraminidase enzyme (50 μl) are placed in a test-tube, along with 50 mM of sodium acetate buffer (pH 5.0), and allowed to react for 5 minutes. 100 μl of 0.125N periodic acid $HIO_4$ (25 mM in $H_2SO_4$) are then added and the reaction is allowed to proceed for 5 more minutes in a heated bath (at 60° C.). At this point, 100 μl of sodium arsenite (1.6% in 0.4N HCl) and 1 ml of 0.1M thiobarbituric acid (pH9 with NaOH) are added to the solution and the resulting solution is heated in a 100° C. bath for 7.5 minutes. A reddish-orange colour will appear. Two ml of extracting solution (acetone and hydrochloric acid) are then added in order to stabilize the colour. A spectrophotometric reading can now be accomplished.

Calculation of the enzymatic activity:

1 neuraminidase unit is defined as the micromols (μmol) of formed NANA per ml and per minute at 37° C., using GDia as the substrate; therefore, the activity of 1 ml of an enzymatic solution may be represented as follows:

$$\text{Unit/ml} = \frac{OD\ NANA \times 20 \times \text{Dilution factor}}{(0.0872) \times (309.28) \times (5)}$$

wherein OD is the optical density of NANA, as measured by the spectrophotometer; 0.0872 is the standard OD obtained from 1 μg of NANA; 309.28 is the molecular weight of NANA and 20 is the standard dilution factor employed according to the present invention. Should a further dilution be carried out, also this latter has to be inserted into the equation.

The specific activity of the enzyme is defined as Unit/mg of protein.

Features of the thus Obtained Enzyme

The neuraminidase obtained by means of the process according to the present invention is characterized by the following features:

1) Functional action

It catalyses the reaction by which a residue of the N-acetyl-neuraminic acid is released from GDia, giving rise to the formation of GM1.

2) Substrate specificity

The enzyme tested had been previoulsy purified according to the procedure previoulsy described.

Thr activity of the neuraminidase obtained according to the present process is highly specific for the alpha configuration of GDia; however it will also catalyse the releasing of NANA from alpha and beta mixtures of the di- and tri-gangliosides as well as from synthetic NANA-lactose, as per the following table:

| Substrate | Relative activity (%) |
| --- | --- |
| GDia alpha 2-3 | 100 |
| GAmix alpha 2-3 alpha 2-6 | 60 |
| NANA-lactose alpha 2-3 alpha 2-6 | 100 |

The neuraminidase obtained according to the present process shows negligible activity towards colominic acid, which is known to have sialic acids linkages of the type alpha 2–8, and collocalia mucoids, which have sialic acids linkages of the type alpha 2–8 and alpha 2–6.

3) Optimum pH

The pH fop optimum activity is 5.0 at a temperature of 37° C. for 5 minutes.

4) Stability

The enzyme is stabile in various organic solvents, like ethanol, methanol and butanol; it shows an increased activity in mixtures of water and organic solvents.

5) Range of optimum temperature (as to activity).

The enzyme is stable at a temperature from 40° to 50° C.; the optimum temperature, as to the enzymatic activity, is 37° C.

6) Enzyme activity and inhibition.

The enzyme has a $K_m$ value approximately equal to $10^{-4M}$ and is strongly inhibited in the presence of NANA. The Ki fop NANA is approximately 0.3 mM.

7) Molecular weight.

The molecular weight of the enzyme tested for substrate specificity, determined by gel permeation chromatography on Sephadex G-100 and by gel electrophoresis (by SDS polyacrilamide electrophoresis, as described by Laemmli in "Cleavage of structural proteins during assembly of the head of bacteriophage T4", Nature, London, 227, pag. 680–685, 1970), shows that the enzyme has a molecular weight of 55,000–60,000.

Variable amounts of the isoenzyme fraction having Molecular Weight 80,000 can be occasionally present as by-product in the crude reactions mixtures and can be separated from the main fraction having molecular weight 55,000–60,000 according to the purification procedure before described.

A neuraminidase sample, prepared according to Uchida et. al (Uchida Y. et al., J. Blochem., 82, 1425–1433, 1977) and analysed under the above mentioned electrophoresis conditions in comparison with the neuraminidase produced according to the present process, showed only a band corresponding to molecular weight 80,000.

It is worth noting that the enzyme produced by Uchida, other than showing a different molecular weight, also shows a different substrate specificity, being active towards colominic acid.

8) Purity.

Neuraminidase is free from toxins and from polluting proteolytic enzymes.

We claim:

1. A process for preparing neuraminidase, comprising the following steps:

a) growing a culture of *Arthrobacter ureafaciens* ATCC 7562 on a solid agar medium in the presence of N-acetyl-neuraminic acid and casein hydrolysate, to obtain a small glossy brilliant colony, herein defined as Arthrobacter Sp.;

b) growing a culture of the above obtained Arthrobacter Sp in a liquid medium containing N-acetyl-neuraminic acid, in a concentration comprised between 0.1 and 1%, and casein hydrolysate;

c) once steady state conditions are reached, the culture of Arthrobacter Sp. is continued under chemostasis conditions, by feeding said culture with a fresh medium which contains N-acetyl-neuraminic acid and is free from casein hydrolysate, to produce neuraminidase;

d) recovering the thus obtained neuraminidase from the media by means of filtration followed by concentration, ultrafiltration, dialysis, and flow through an ion exchange resin.

2. The process as claimed in claim 1, wherein the small glossy brilliant colony of Arthrobacter Sp is isolated after 24 hours of growth on the solid medium.

3. The process as claimed in claim 2, wherein in step a) pH is comprised between 7.0 and 7.5 and the temperature is comprised between 25° and 30° C.

4. The process as claimed in claim 1, wherein the culture of Arthrobacter Sp. during steps b) and c) is effected under stirring-aeration conditions, at pH values comprised between 7.0 and 7.5 and at temperatures between +20° C. and +30° C.

5. The process as claimed in claim 1, wherein steps b) and c) are carried out at pH 7.3, and at a temperature of 26° C.

6. The process as claimed in claim 1, wherein the concentration of N-acetyl-neuraminic acid during step b) prior to reaching steady state conditions is comprised between 0.1 and 1% w/v, and the concentration of casein hydrolysate is comprised between 0.1 and 0.5% w/v, and in step c) after reaching steady state conditions the concentration of N-acetyl-neuraminic acid during step c) varies from 0.05 to 1%.

7. The process as claimed in claim 1, wherein in step b) the Arthrobacter Sp is inoculated in an amount to provide an initial optical density of the cellular suspension of 0.1–0.2 Optical Density units.

8. The process as claimed in claim 1, wherein steady state conditions are reached in step b) when the optical density of the cells in reaction medium reaches values comprised between 1.5 to 4 Optical Density units, and during step c) after reaching steady state conditions said fresh medium is fed into the reaction vessel at a rate so as to maintain the optical density between 3 and 5 Optical Density units.

9. The process as claimed in claim 1, wherein the process prior to reaching steady state conditions is carried out using as the growing medium for Arthrobacter Sp. an aqueous solution containing casein hydrolysate and N-acetyl-neuraminic acid as the only carbon sources and the process after reaching steady state conditions is carried out using during step c) a fresh medium containing yeast extract other than N-acetyl-neuraminic acid as the organic nutrients.

10. The process as claimed in claim 9, wherein prior to reaching steady state conditions, the concentrations of casein hydrolysate and N-acetyl-neuraminic acid are both 0.5% and in the process during step c) after reaching steady conditions the N-acetyl-neuraminic acid is 0.5% and the concentration of the yeast extract is 0.4%; both in step b) and c) the pH is 7.3 and the temperature is 26° C.

11. The process as claimed in claim 9, wherein steady state conditions are reached at the end of step b) when the optical density of the cells in the medium is comprised between 2.0–2.5 and during step c), after reachinq steady state conditions, the fresh medium is fed when the optical density fluctuates between 1.4 and 2.5, and it is pumped into the reaction vessel at a flow rate so as to maintain the optical density between 4 and 5 Optical Density units [O.D].

12. The process as claimed in claim 9, wherein the fresh medium is fed at a flow rate comprised between 27 to 35 ml/min.

13. The process as claimed in claim 1, wherein the filtration is carried out on a membrane of cellulose acetate having a pore diameter of 0.2 μm; the concentration is effected through a cellulose acetate membrane showing a molecular cut-off of 10,000 daltons; the dyalisis is effected against a pH 5.3 acetate buffer; and the ion exchange resin is a resin of dextran cross-linked with epichlorohydrin, functionalised with carboxymethyl groups and with an exclusion molecular weight limit of $2 \times 10^5$, balanced to pH 5.3 with an acetate buffer.

* * * * *